(12) United States Patent
Presswood et al.

(10) Patent No.: US 10,380,271 B2
(45) Date of Patent: Aug. 13, 2019

(54) METHOD AND APPARATUS FOR DENTAL ARTICULATION

(71) Applicants: Ronald G. Presswood, Houston, TX (US); Ronald G. Presswood, Jr., Houston, TX (US)

(72) Inventors: Ronald G. Presswood, Houston, TX (US); Ronald G. Presswood, Jr., Houston, TX (US)

( * ) Notice: Subject to any disclaimer, the term of this patent is extended or adjusted under 35 U.S.C. 154(b) by 770 days.

(21) Appl. No.: 14/377,264

(22) PCT Filed: Feb. 13, 2013

(86) PCT No.: PCT/US2013/025954
§ 371 (c)(1),
(2) Date: Aug. 7, 2014

(87) PCT Pub. No.: WO2013/123062
PCT Pub. Date: Aug. 22, 2013

(65) Prior Publication Data
US 2015/0019176 A1    Jan. 15, 2015

Related U.S. Application Data

(60) Provisional application No. 61/598,708, filed on Feb. 14, 2012.

(51) Int. Cl.
*G06F 17/50* (2006.01)
*A61C 9/00* (2006.01)
*A61C 11/00* (2006.01)
*A61C 13/00* (2006.01)
*A61C 7/00* (2006.01)
*G16H 20/40* (2018.01)

(52) U.S. Cl.
CPC .............. *G06F 17/50* (2013.01); *A61C 7/002* (2013.01); *A61C 9/004* (2013.01); *A61C 9/0053* (2013.01); *A61C 11/00* (2013.01); *A61C 13/0004* (2013.01); *G16H 20/40* (2018.01)

(58) Field of Classification Search
CPC ...................................................... G06F 17/50
USPC ............................................................ 703/1
See application file for complete search history.

(56) References Cited

U.S. PATENT DOCUMENTS

| | | | |
|---|---|---|---|
| 9,526,599 B2 * | 12/2016 | Kadobayashi | A61C 11/00 |
| 2002/0150859 A1 | 10/2002 | Imgrund | |
| 2011/0191081 A1 * | 8/2011 | Malfliet | A61C 11/00 |
| | | | 703/11 |
| 2011/0276159 A1 | 11/2011 | Chun et al. | |

(Continued)

OTHER PUBLICATIONS

European Patent Office, Search Report, Appn: 13749906.7; PCT/US2013025954, dated Aug. 21, 2015 (2 publications).

(Continued)

*Primary Examiner* — Andy Ho
(74) *Attorney, Agent, or Firm* — Frost Brown Todd LLC

(57) ABSTRACT

This invention relates to improved methods and apparatus for recording and simulating the condylar movement of an individual. This invention also provides a digital dental articulator method which is designed to simulate the jaw or condylar movements of a patient. This instrument enables a dentist to obtain the necessary diagnostic information for treatment of the occlusal irregularities, such as malocclusion, and the fabrication of dental restorations or "dentures" and for the development of an orthodontic treatment plan.

8 Claims, 4 Drawing Sheets

(56) References Cited

U.S. PATENT DOCUMENTS

2013/0066598 A1* 3/2013 Fisker .................... A61C 11/00
                                                          703/1
2013/0204600 A1* 8/2013 Mehra ................. G06F 19/3437
                                                          703/11

OTHER PUBLICATIONS

Australian Patent Examination Report No. 1; Appn: 2013221673; dated Jun. 27, 2016 (2 publications).
New Zealand; First Examination Report; IP No. 628271; dated Dec. 8, 2014 (no references).

* cited by examiner

METHOD AND APPARATUS FOR DENTAL ARTICULATION

TECHNICAL FIELD

The present invention relates to an improved method to manufacture dental appliances or solve for the final alignment of a patient's teeth after a patient undergoes an orthodontic procedure. The term appliances refers to any type of apparatus that can be used for repairing, adjusting or replacing one or more teeth of a patient such as, but not limited to, bridges, crowns, arches, dentures and braces or all kinds. The invention utilizes a mathematical approach within a Computer Aided Design (CAD) system to generate a unique articulation method. The mathematics generate a dynamic articulation within the CAD software from the wear surfaces of the patient's teeth surfaces or from a unique tool based on information from a patient's generated rim bite, called "Eric's Rim," which is described in pending U.S. Patent Application No. US2011/032674, which is incorporated herein as though fully set forth. In accordance with the invention, once this articulation has been created in a digital model, it can then be used to solve for the patient's occlusal function. This occlusal function can be used to engineer a restoration based on the materials prescribed by the dentist or solve for the tooth alignment at the completion of an orthodontic procedure.

BACKGROUND OF THE INVENTION

Currently, Computer Aided Design (CAD) dentistry utilizes either a set of impression trays to make a mold of a patient's teeth or dental arch, which is filled with plaster to create a model of the patient's teeth. The plaster model of the patient's teeth is then scanned using a 3D laser scanner, or optionally an intraoral 3D scanning system can be utilized to create a digital 3D model of the patient's teeth or dental arch. The digital models of the upper and lower dental arch within the CAD program are then "mounted" in a digital representation of a dental articulator to allow the dentist or dental technician to design a crown or bridge or orthodontic procedure. These articulators are simply digital copies of the physical articulators currently on the market. The dentists or the dental technician then creates the CAD dental restoration, crown or bridge, or an orthodontic procedure to align the patient's teeth. For dental restorations, the CAD program will utilize a library of teeth, in some cases up to 300 different tooth models to design a crown or multiple teeth to design a bridge or full upper or lower dental arch. Once completed, the restoration is sent to a milling lab to be manufactured. Once milled, the restoration is returned to the dentist for "try-in" and fitting. This fitting requires the dentist to match the restoration to the patient's jaw movements and dental function or occlusion. For an orthodontic procedure, the digital dental model is separated into the patient's individual teeth, and the teeth are then moved in incremental steps until the ultimate alignment is achieved. FIG. 1 is representative of a typical Dental CAD system comprised of a 3-D Laser Scanner 10 and a computer workstation which includes a computer 12, monitor 14 and keyboard 16. FIG. 3 shows digital model of a typical dental articular which is used to hold models of an upper dental arch 127 and a lower dental arch 137 and allow the user to simulate the movement of the jaw when fabricating dental restorations such as crowns, bridges, and dentures. Use of a virtual articulator in conjunction with the invention is described in greater detail below.

The purpose of a dental articulator is to simulate the jaw or condylar movements of a patient. This instrument enables a dentist to verify the contact points between opposing teeth for dental restorations such as a crown or bridge or, for orthodontics, the contact points of the tooth surfaces themselves. FIG. 2 is representative of standard articulator used within the dental industry, which includes upper and lower frame sections 20, 22, which hold an articulating model formed from casts or impressions of the upper and lower teeth of a patient (not shown), respectively. The upper frame section is mounted to rotate about an axis 24, linearly relative to the lower frame section. An adjustable rod 26 can be used to maintain spacing the operator deems to be appropriate between the upper and lower teeth.

U.S. Pat. No. 7,412,298 issued to the inventors herein, entitled "Method and System for Morphometric Analysis of Human Dental Occlusal Function and Uses Thereof" (hereinafter referred to as "the '298 Patent"), demonstrates a mathematical method for analyzing jaw motion by calculating the shape of Temporomandibular Joint (TMJ) from the wear surfaces of at least two teeth of the patient's upper or lower jaw. The same mathematical method can be used to solve for the individual's dynamic occlusal function if the shape of the TMJ has previously been solved using the U.S. Pat. No. 7,412,298, or has been measured using a scanning method such as a CAT Scan. Pending U.S Patent application US2011/032674 demonstrates a method for creating dental restorations in a similar analog method, this method can be used to make a single crown, partials, bridges or full dental arches, or develop a orthodontic treatment. This patent describes a method to manufacture dental restorations for an edentulous patient using "Eric's Rims" to record the patient's dynamic occlusion. All of the mathematical formulations and details of the methods disclosed in U.S. Pat. No. 7,412,298, and the details for using Eric's Rims in pending application US2011/032674, are incorporated herein as though fully set forth.

While there are multiple commercially available CAD systems for the manufacture of Dental Restorations and for the development of orthodontic treatment plans, and while these methods have been available for some time, the methods employed do not attempt to record or calculate each patient's particular TMJ or dynamic occlusal function. The systems currently in place utilize digital models of linear articulators, of the type shown in FIG. 2, which create a linear duplication of the condylar guidance, or rely on the static contact of the upper and lower teeth to design the contact of wear surfaces.

Thus, there is a need for an advanced method to replicate accurately the unique path of motion of a patient's dynamic occlusion when creating a dental restoration in a CAD system.

BRIEF SUMMARY OF THE INVENTION

The present invention is directed to an improved method for making CAD-designed dental restorations, preparation guides or implant guides for restorations or orthodontic treatment plans, the tools used to make these restorations, and to a method of creating a patient specific dental articulator within a CAD program and, more particularly, to an improved digital articulator which allows for accurate simulation of the jaw or condylar movements of a patient and accurate interchangeability of digital representations of a patients dental casts.

This process is unique in at least two aspects relating to common dental practice: (1) there is an expectation of calculating the balancing (non-working side) guides for registering the medial wall of the glenoid fossa; and (2) all guidance is patient initiated and calculated from the wear surfaces on the patient's teeth or from patient generated bite rims or "Eric's Rims" when the patient has no teeth, which are described in U.S Patent application US2011/032674.

In the present invention, an improved digital dental articulation method is described. A dental articulator includes a digital or virtual model of an upper frame and a lower frame for simulating the lower dental arch and the upper dental arch, one of the frames having a pair of condyles mounted thereon, and a pair of digitally adjustable condylar tables mounted on the other of the frames.

In accordance with another aspect of this invention, there is provided a method of calculating three-dimensional jaw movements and transferring the record to a digital representation of a dental articulator, comprises the steps of: (1) producing a standard impression of a patient's dentition or a standard model of the patient's upper dental arch and lower dental arch; (2) scanning the impression or model of the upper arch and lower arch using a 3D laser scanner; (3) importing the scans into a CAD system; (4) identifying the occlusal wear surfaces on the tooth surfaces either manually or automatically within the CAD program; (5) utilizing the math described in the U.S. Pat. No. 7,412,298 to calculate guiding surfaces for the TMJ for the dental restoration, be it for posterior teeth, the bicuspid teeth or the anterior or incisor teeth. This method will allow for changes in tooth height so that the CAD Operator, which may be a dentist, a Certified Dental Technician, or other designer, can open or close the patient's bite while still maintaining the appropriate occlusal form. Once the guide surfaces of the tooth or teeth, have been calculated, the restoration can be engineered to the material properties of the material(s) chosen by the Dentist. Preparation guides can be created to assist the Dentist when preparing the tooth or teeth for restoration. The preparation guide will assist the Dentist in removing the least amount of the natural dentition of the tooth or teeth to be restored. Bone level implant guides can be created to assist the dentist with the correct spatial placement of the implants.

In accordance with another aspect of this invention, there is provided a method whereby digital scans are captured utilizing an intraoral scanner as opposed to capturing a scan of the impression of the patient's dentition.

In accordance with other aspects of this invention, there is provided a method whereby the digital scans are used to create an orthodontic treatment plan, to develop a plan to determine the proper placement of the bicuspids and molars to keep them in proper occlusal function with an individual patient's TMJ.

The foregoing outlines rather broadly the features and technical advantages of the present invention in order that the detailed description of the invention that follows may be better understood. Additional features and advantages of the invention will be described hereinafter which will form the subject of the claims of the invention. It should be appreciated by those skilled in the art that the conception and specific embodiment disclosed may be readily utilized as a basis for modifying or designing digital methods for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying Figures. It is to be expressly understood, however, that each of the Figures is provided for the purpose of illustration and description only and is not intended as a definition of the limits of the present invention.

BRIEF DESCRIPTION OF THE DRAWINGS

For a more complete understanding of the present invention, reference is now made to the following description taken in conjunction with the accompanying Figures and drawings, in which.

DETAILED DESCRIPTION OF THE INVENTION

As used herein, "a" or "an" means one or more than one.

The methods and apparatus of the present invention will now be illustrated with reference to FIGS. 1 through 4. It should be understood, that these are merely illustrative and not exhaustive examples of the scope of the present invention and that variations which are understood by those having ordinary skill in the art are within the scope of the present invention.

Figure 1:
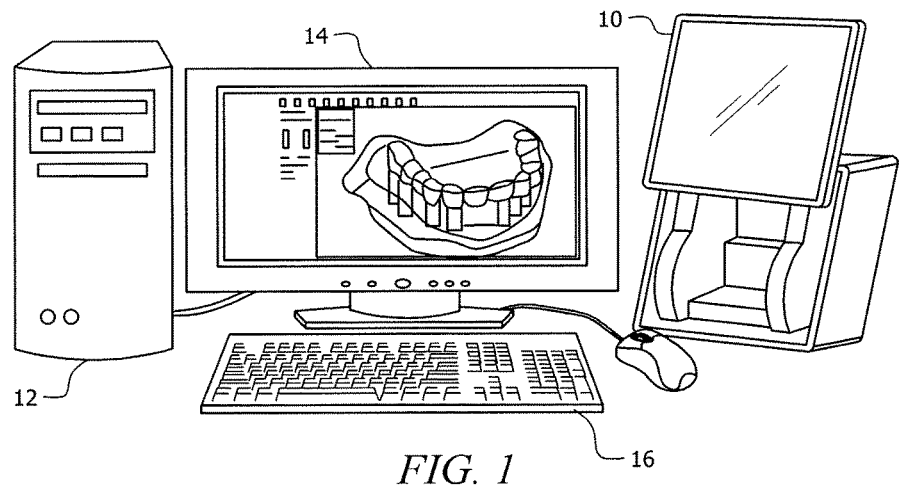
FIG. 1 shows a typical Dental CAD system with scanner and computer work station.
Figure 2:
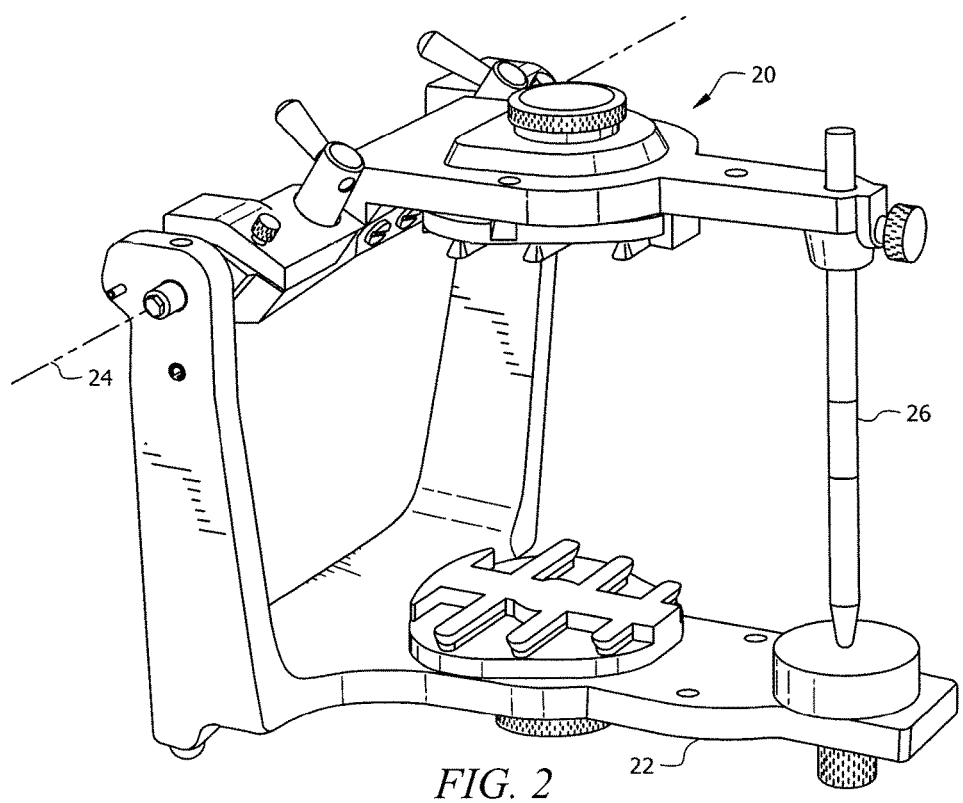
FIG. 2 shows a typical dental articulator.
Figure 3:
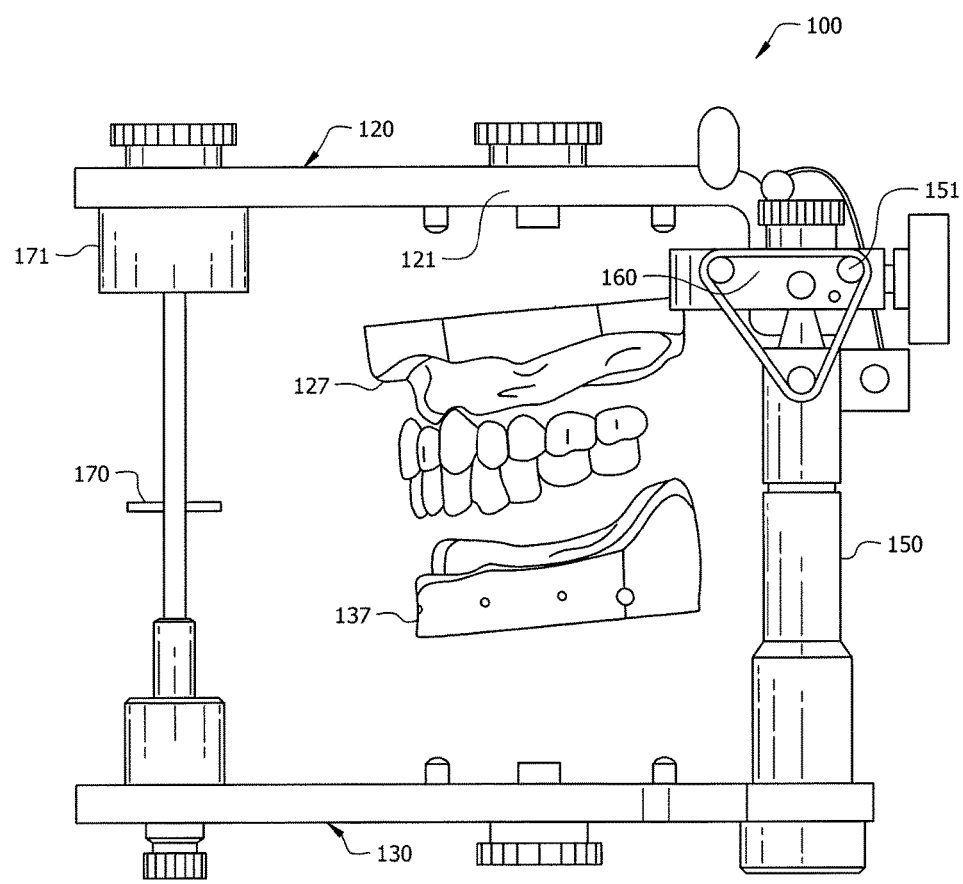
FIG. 3 shows the details of a typical dental articulator as part of a digital image.

Referring to FIG. 3, an example of a dental articulator is shown, which is part of a digital image on a computer screen. The dental articulator can be used to hold models of an upper dental arch 127 and a lower dental arch 137 and allow the user to simulate the movement of the jaw when fabricating dental restorations such as crowns, bridges, and dentures.

The digital dental articulator 100 has an upper frame 120 and lower frame 130, which are used to mount the models of the upper dental arch 127 and lower dental arch 137, respectively. The model of the upper dental arch 127 is held to the arm 121 of upper frame 120 by a digital attachment, or digital spacer. The spacer fixes the models at the midplace between the upper and lower frames. The position of the upper dental arch 127 can be adjusted within the CAD program by the CAD operator. Dental articulator 100 has a pair of posts 150 with condyles 151. Only one post 150 is shown because of the angle of the figure, but a second post is hidden by the one shown. Condyle 151 fits with condylar table 160 to simulate the temporal mandible joint of the patient. The condyle can be any shape the can be used accurately to represent the motion of the of the patient's jaw. However, most conventional dental articulators use a spherical shaped member.

Figure 4:
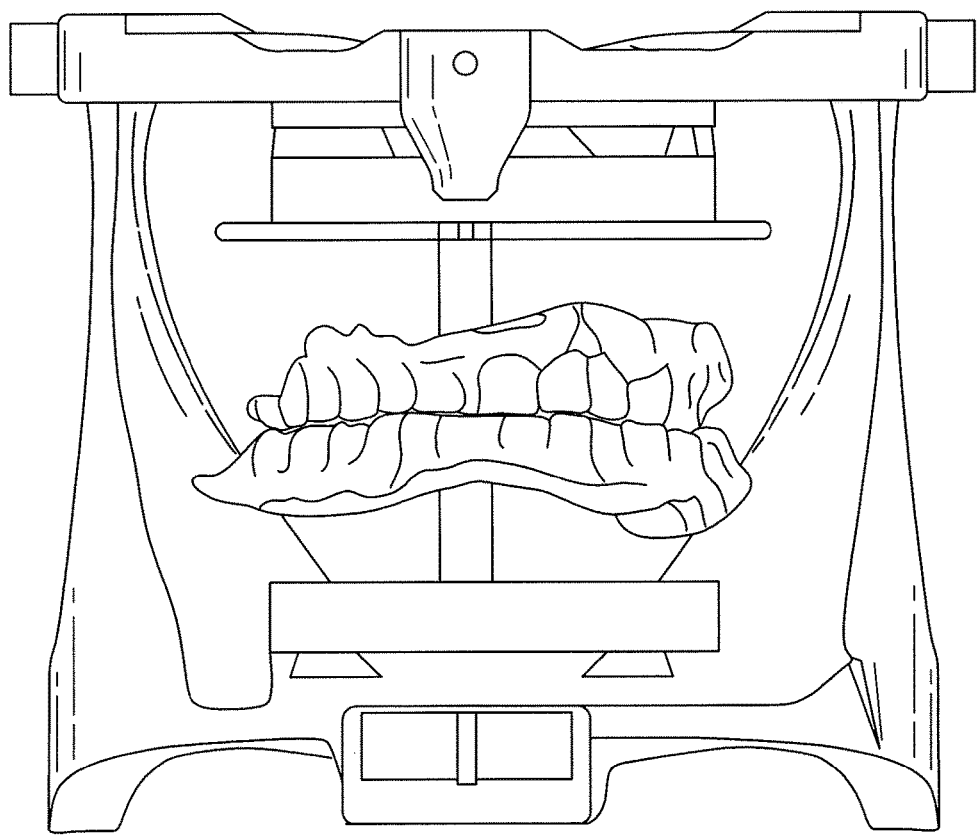
FIG. 4 shows a virtual dental articular as viewed by a CAD operator.

FIG. 4 shows a virtual image of a dental articulator of the type shown in FIG. 3, which illustrates how a CAD operator would see it.

Within the CAD program, the condylar table 160 is modeled to create the wear surface of the TMJ or "Zola's Tubercle". The shape of this wear surface is calculated using the mathematical formulas and methods described in U.S. Pat. No. 7,412,298. The wear surface will recreate the functional dynamics of the patient's jaw within the CAD system. These mathematical formulas for each patient, once created, can be stored for future reference.

Dental articulator 100 also has an incisal pin 170 and incisal table 171. Incisal pin 170 is utilized to set the normal distance between the upper dental arch 127 and the lower dental arch 137.

The digital dental articulator can be used to make dental restorations, dentures and design an orthodontic treatment plan. The procedure for using the improved dental articulator is described in further detail below.

Figure 5:
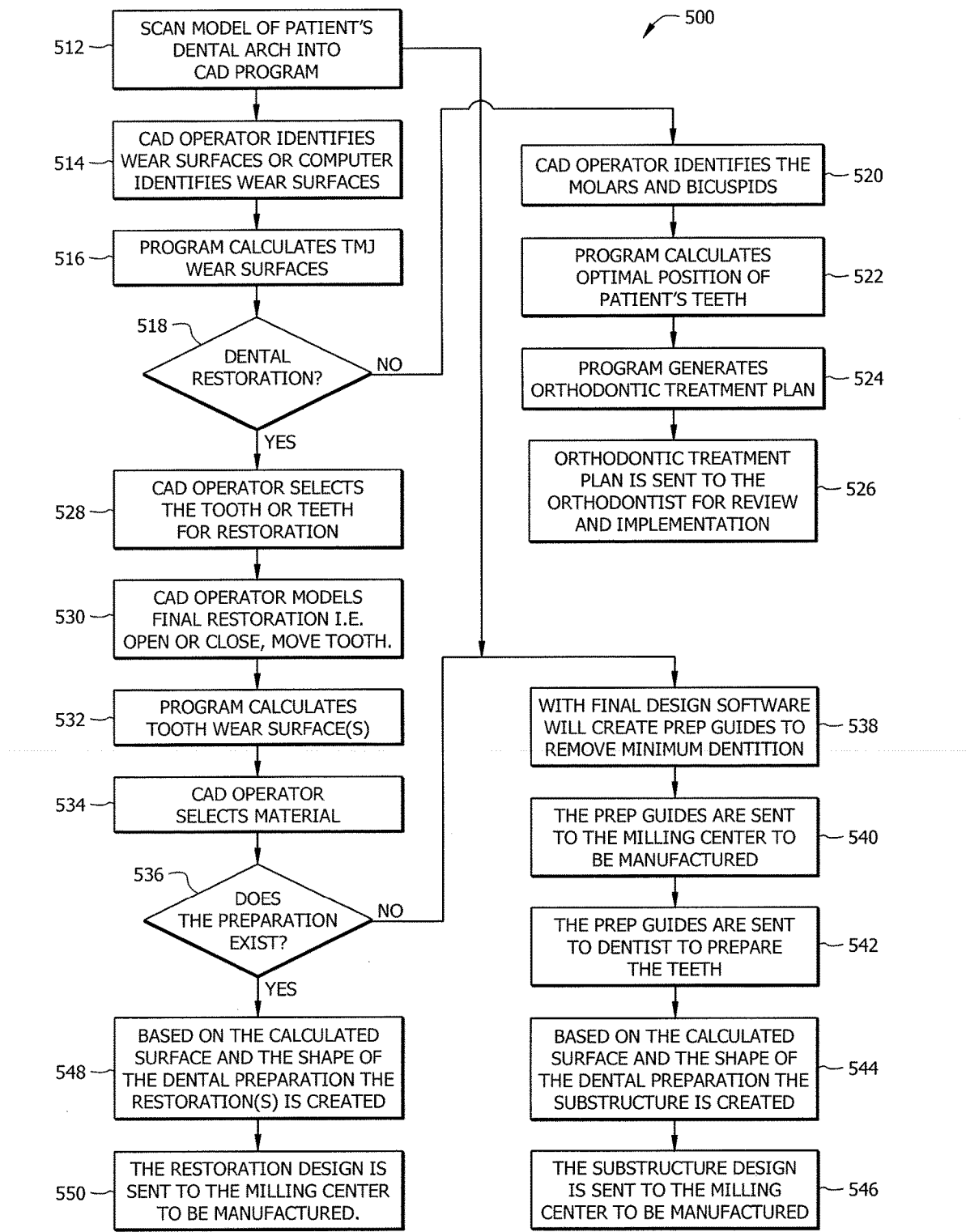
FIG. 5 is a flow chart of the software architecture of the current invention.

Turning now to FIG. 5, which is a general flow chart of the software, the digital dental articulator can be used to make dental restorations, such as crowns and bridges, using the any of following methods: (1) prepare the teeth for restoration; make an impression of the teeth; produce the upper and lower model of the teeth; scan the upper and lower models of the teeth 410; the CAD operator or the program will identify the wear surfaces of the teeth 412 and, using the mathematical formulas described in the U.S. Pat. No. 7,412,298, calculate the guiding surface of the TMJ 414; CAD Operator selects the tooth or teeth to be restored 432, CAD Operator can modify the bite 434 and then use the formulas described in U.S. Pat. No. 7,412,298 to solve for the wear surfaces of the restorations 436; using the material properties of the materials prescribed by the dentist 438, engineer the restoration and/or the substructure 462; and send the restoration to the milling lab to be manufactured 464; or (2) prepare the teeth for restoration; produce an intraoral scan of the patient's upper and lower teeth 410; the CAD Operator or the program will identify the wear surfaces of the teeth 412 and, using the mathematical formulas described in U.S. Pat. No. 7,412,298 to calculate the guiding surface of the TMJ 414, the CAD Operator selects the tooth or teeth to be restored 432; the CAD Operator can modify the bite 434 then use the formulas described in U.S. Pat. No. 7,412,298 to solve for the wear surfaces of the restorations 436; using the material properties of the materials prescribed by the dentist 438, engineer the restoration and/or the substructure 462; send the restoration to the milling lab to be manufactured 464; (3) make an impression of the teeth; produce the upper and lower model of the teeth; scan the upper and lower models of the teeth 410; the CAD Operator or the program will identify the wear surfaces of the teeth 412 and, using the mathematical formulas described in U.S. Pat. No. 7,412,298 to calculate the guiding surface of the TMJ 414; CAD Operator selects the tooth or teeth to be restored 432; CAD Operator can modify the bite 434 then use the mathematical formulas described in U.S. Pat. No. 7,412,298 to solve for the wear surfaces of the restorations 436; using the material properties of the materials prescribed by the dentist 438, and using the design of the restoration to create preparation or prep guides for the dentist 444, the preparation guides are sent to be manufactured 446; the dentist uses the preparation guides to remove the natural dentition from the patients tooth or teeth to be restored 448; steps 1 or 2 can be employed to create the restoration 470; (4) produce an intraoral scan the upper and lower teeth; 410; the CAD Operator or the program will identify the wear surfaces of the teeth 412 and using the mathematical formulas described in U.S. Pat. No. 7,412,298 to calculate the guiding surface of the TMJ 414; CAD Operator selects the tooth or teeth to be restored 432; CAD Operator can modify the bite 434 then use the mathematical formulas described in U.S. Pat. No. 7,412,298 to solve for the wear surfaces of the restorations 436; using the material properties of the materials prescribed by the dentist 438 and using the design of the restoration to create preparation or prep guides for the dentist 444; the preparation guides are sent to be manufactured 446; the dentist uses the preparation guides to remove the natural dentition from the patients tooth or teeth to be restored 448, steps 1 or 2 are employed to create the restoration 470; (5) for an orthodontic procedure, the dentist makes an impression of the teeth producing the upper and lower model of the teeth; scan the upper and lower models of the teeth 410; using the formulas described in U.S. Pat. No. 7,412,298 to calculate the guiding surface of the TMJ 412; the CAD operator or the programmer identifies the wear surfaces of the teeth 412 and using the formulas described in U.S. Pat. No. 7,412,298 to calculate the guiding surface of the TMJ 414; the CAD operator identifies the molar and bicuspid wear surfaces 422 then uses the formulas described in U.S. Pat. No. 7,412,298 to solve final position and orientation of the patient's teeth passed on the buckle cusp's of the molars and bicuspids 424; engineer the treatment plan to the orthodontist to move the patient's teeth to allow for the proper final placement of the buccal cusp's of the molar's and bicuspids 426; send the treatment plan to the Orthodontist for review and implementation 428; or (6) the orthodontist produces an intraoral scan of the upper and lower teeth; 410; using the formulas described in U.S. Pat. No. 7,412,298 to calculate the guiding surface of the TMJ 412, the CAD operator or the program will identify the wear surfaces of the teeth 412; using the formulas described in U.S. Pat. No. 7,412,298 to calculate the guiding surface of the TMJ 414, the CAD operator identifies the molar and bicuspid wear surfaces 422; use the formulas described in U.S. Pat. No. 7,412,298 to solve final position and orientation of the patient's teeth placement on the buccal cusp's of the molars and bicuspids 424; engineer the treatment plan to the orthodontist to move the patient's teeth to allow for the proper final placement of the buccal cusps of the molar's and bicuspids 426; send the treatment plan to the Orthodontist for review and implementation 428. Further details for these methods are described below.

The following describes the method of the present invention for the restoration of a tooth, specifically the preparation of a crown. However, those skilled in the art will understand that this method can be applied to any dental restoration procedure and is particularly useful in restorations involving multiple teeth or restorations where a terminal tooth is missing.

The first step in applying the present invention requires the preparation of the tooth for the restoration. Generally, the preparation of a tooth for a crown involves the irreversible removal of a significant amount of tooth structure. When preparing a tooth for a crown, typically, the enamel is totally removed and the finished preparation is, thus, entirely dentin. The amount of tooth structure required to be removed will depend on the material(s) being used to restore the tooth. For example, if porcelain is applied to a metal or ceramic substructure, the entire tooth is reduced a minimum of 1.5 mm. It is an option within the scope of this process for the dentist to request from the technician or the CAD operator a set of preparation guides, these preparation guides will assist the dentist in removing the least amount of the dentition. The CAD operator will use the models or scans provided by the dentist and the CAD software to create a preliminary restoration that will allow for the creation of the preparation guides. This same process for creating preparation guides can be employed to create a restoration plan to place bone level implants.

After the tooth is prepared, a standard impression of the dentition is made, allowing accurate models of the teeth to be made later. An impression is carried out by placing a putty material into the mouth in a customized tray. The material then sets (hardens) to become an elastic solid, and when removed from the mouth, retains the shape of the teeth. Common materials used for dental impressions include, but are not limited to, sodium alginate, agar, condensation-cured silicones, and addition-cured silicones such as polyvinyl siloxane. The impressions are then used to generate the models of the patient's teeth. Models of the upper and lower dental arches are then scanned using a 3D laser scanner or other scanning method. These scans are then transferred or imported into the dental CAD program. An alternative method is to directly scan the natural and prepared dentition and import these scans into the CAD program.

Once the models of the upper and lower dental arches are scanned and imported into the CAD program, either the CAD operator or the CAD software will identify the wear surfaces of the teeth of either the upper or lower arch. The software will then solve for the guiding surfaces of the TMJ or "Zola's Tubercle". Once solved, the CAD operator will then identify the teeth for which the restoration will be created. The software will then calculate the wear surface of the tooth or teeth to be designed. The models can be "mounted" in the digital articulator to simulate the movement of the patients jaw function so as to verify the occlusal function.

The digital dental articulator can also be used to make dentures or full restorations for edentulous patients, or those who have no teeth. The steps to make dentures or full restorations using the improved dental articulator are similar to the steps used to make dental restorations, except the patient's occlusal function is recorded using Eric's Rims. The method of using Eric's Rims is disclosed in pending US Patent Application US2011/032674. Once the occlusal function is created using Eric's Rims, a 3-D scan of the rims is created using a 3-D scanner. The scans are then imported into the CAD program. The software will then solve for the guiding surface of the TMJ or "Zola's Tubercle". The software then can place the teeth into function to meet the patient's occlusal function for either the denture or the full restoration.

Once the dental restorations have been designed within the CAD software, they will be sent to be manufactured or milled. After they are manufactured they will be returned to the dentist for placement, i.e., "seating".

Generally, the digital dental articulator can be used to develop a orthodontic treatment plan, using the either of following steps: making an impression of the teeth; producing the upper and lower model of the teeth; scan the upper and lower models of the teeth; using the mathematical formulas described in the U.S. Pat. No. 7,412,298 to calculate the guiding surface of the TMJ; using the mathematical formulas described in the U.S. Pat. No. 7,412,298 to develop the treatment plan to determine the placement of the bicuspids and molars to keep them in proper occlusal function with that individual patient's TMJ. Alternatively, the digital dental articular can be used with the following procedure: preparing the teeth for restoration; producing an intraoral scan of the upper and lower models of the teeth; using the mathematical formulas described in the U.S. Pat. No. 7,412,298 to calculate the guiding surface of the TMJ; using the mathematical formulas described in the U.S. Pat. No. 7,412,298 to develop the treatment plan to determine the placement of the bicuspids and molar to keep them in proper occlusal function with that individual patient's TMJ.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A method for preparing a dental appliance for a dental patient by using a computer with a program that includes a digital dental articulator apparatus, comprising the steps of:
   a. creating a digital model of the patient's upper and lower teeth;
   b. using the computer for digitally mounting the model in the digital dental articulator;
   c. using the computer for calculating, using Eric's rims, the guiding surfaces of the patient's temporomandibular joints by using occlusal wear surfaces between the patient's upper and lower teeth; and
   d. preparing the dental appliance by using the information obtained from step c.

2. The method of claim 1, where the step of calculating a guiding surfaces comprises scanning a physical model of the teeth to create the digital image.

3. The method of claim 1, wherein the step of calculating the guiding surfaces comprises using an intraoral scan of the models of the upper and lower teeth.

4. The method of claim 1 wherein the dental appliance comprises a bridge, crown, full arch, braces or any apparatus for adjusting the teeth.

5. The method of claim 1, where the step of calculating the guiding surfaces comprises:
   creating a physical model of the teeth;
   scanning the physical model to create a digital image of the model; and
   calculating the guiding surfaces using the scanned model.

6. The method of claim 1, wherein the step of creating a digital model of the patient's upper and lower teeth comprises:
   using an intraoral scan of the models of the upper and lower teeth;
   and generating the digital model of the teeth.

7. The method of claim 6, wherein the step of calculating the guiding surfaces further comprises calculating the guiding surfaces using the generated digital model.

8. A method for preparing a dentures for a dental patient by using a computer with a program that includes a digital dental articulator apparatus, comprising the steps of:
   a. creating a digital model of the patient generated bite rims, i.e., Eric's Rims;
   b. digitally mounting the digital bite rims in the digital dental articulator;
   c. calculating the guiding surfaces of the patient's Temporomandibular joints by using occlusal wear surfaces between the patient generated bite rims;

d. preparing dentures by using the information obtained from step c.

\* \* \* \* \*